US012794716B1

(12) United States Patent
Creek et al.

(10) Patent No.: US 12,794,716 B1
(45) **Date of Patent: *Nov. 10, 2026**

(54) COMPRESSED PKI METHODS FOR MACHINE-TO-MACHINE AUTHENTICATION IN BANDWIDTH-CONSTRAINED MEDICAL DEVICES

(71) Applicant: Advanced Neuromodulation Systems, Inc., Plano, TX (US)

(72) Inventors: Greg Creek, Prosper, TX (US); Steve Gray, McKinney, TX (US); Daran DeShazo, Lewisville, TX (US); Luis Ortiz Hernandez, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 36 days.

This patent is subject to a terminal disclaimer.

(21) Appl. No.: 18/936,913

(22) Filed: Nov. 4, 2024

Related U.S. Application Data

(63) Continuation of application No. 17/982,853, filed on Nov. 8, 2022, now Pat. No. 12,177,367.

(Continued)

(51) Int. Cl.
*H04L 9/32* (2006.01)
*G16H 40/67* (2018.01)

(52) U.S. Cl.
CPC ........... *H04L 9/3268* (2013.01); *G16H 40/67* (2018.01); *H04L 9/3247* (2013.01)

(58) Field of Classification Search
CPC ...... H04L 9/3268; H04L 9/3247; G16H 40/67
See application file for complete search history.

(56) References Cited

U.S. PATENT DOCUMENTS

| | | | | |
|---|---|---|---|---|
| 6,981,139 | B2 * | 12/2005 | Enokida | H04L 63/12 713/169 |
| 7,212,110 | B1 | 5/2007 | Martin et al. | |

(Continued)

FOREIGN PATENT DOCUMENTS

| | | | |
|---|---|---|---|
| WO | 0193953 | A1 | 12/2001 |

OTHER PUBLICATIONS

Schu, S. et al., “A Prospective, Randomised, Double-blind, Placebo-controlled Study to Examine the Effectiveness of Burst Spinal Cord Stimulation Patterns for the Treatment of Failed Back Surgery Syndrome,” Neuromodulation: Technology at the Neural Interface, vol. 17, No. 5, Jul. 2014, pp. 443-450, ScienceDirect.

(Continued)

*Primary Examiner* — Chau Le
(74) *Attorney, Agent, or Firm* — Norton Rose Fulbright US LLP

(57) ABSTRACT

Embodiments provide methods of conducting operations with an implantable medical device (IMD) and an external controller device for performing authentication operations. In some embodiments, the method comprises: generating or storing an authentication data structure in the external controller device for over-the-air communication between the external device and the IMD, wherein the authentication data structure is generated by: (1) removing attribute fields from a first digital certificate and adding a public key of the external controller device to form an intermediate data structure; (2) creating a digital signature of the first intermediate data structure using a second digital certificate of an issuing certificate authority (CA); and (3) forming the authentication data structure by combining the intermediate data structure, the created digital signature, a public key of the issuing CA, and a digital signature of the public key of (Continued)

the issuing CA created using a third digital certificate of a root CA.

20 Claims, 7 Drawing Sheets

Related U.S. Application Data

(60) Provisional application No. 63/276,920, filed on Nov. 8, 2021.

(56) References Cited

U.S. PATENT DOCUMENTS

| | | | |
|---|---|---|---|
| 7,228,179 | B2 | 6/2007 | Campen et al. |
| 7,571,007 | B2 | 8/2009 | Erickson et al. |
| 8,224,453 | B2 | 7/2012 | De Ridder |
| 8,682,441 | B2 | 3/2014 | De Ridder |
| 2018/0183592 | A1 | 6/2018 | Campagna et al. |
| 2018/0183602 | A1 | 6/2018 | Campagna et al. |
| 2018/0183774 | A1 | 6/2018 | Campagna et al. |
| 2020/0398062 | A1* | 12/2020 | Ibarrola ............ A61N 1/37254 |
| 2020/0398063 | A1 | 12/2020 | DeBates et al. |
| 2023/0100246 | A1 | 3/2023 | DeBates et al. |

OTHER PUBLICATIONS

Al-Kaisy, A. et al., "Sustained Effectiveness of 10 kHz High-Frequency Spinal Cord Stimulation for Patients with Chronic, Low Back Pain: 24-Month Results of a Prospective Multicenter Study," Pain Medicine,, vol. 15, 2014, pp. 347-354, Wiley Periodicals, Inc.

Sweet, J. et al., "Paresthesia-Free High-Density Spinal Cord Stimulation for Postlaminectomy Syndrome in a Prescreened Population: A Prospective Case Series," Neuromodulation: Technology at the Neural Interface, vol. 19, No. 3, Apr. 2016, pp. 260-267, ScienceDirect.

Tass, P. A., et al., "Coordinated reset has sustained aftereffects in Parkinsonian monkeys," Annals of Neurology, vol. 72, No. 5, pp. 816-820, John Wiley & Sons, Inc., Published 2012.

* cited by examiner

COMPRESSED PKI METHODS FOR MACHINE-TO-MACHINE AUTHENTICATION IN BANDWIDTH-CONSTRAINED MEDICAL DEVICES

PRIORITY

The present application is a continuation of U.S. application Ser. No. 17/982,853, filed Nov. 8, 2022, and entitled "COMPRESSED PKI METHODS FOR MACHINE-TO-MACHINE AUTHENTICATION IN BANDWIDTH-CONSTRAINED MEDICAL DEVICES," which claims the benefit of and priority to U.S. Provisional Application No. 63/276,920, filed Nov. 8, 2021, and entitled "COMPRESSED PKI METHODS FOR MACHINE-TO-MACHINE AUTHENTICATION IN BANDWIDTH-CONSTRAINED MEDICAL DEVICES," the contents of which are incorporated herein by reference in their entirety.

BACKGROUND

Implantable medical devices have improved medical care for patients with certain types of chronic illnesses and disorders. For example, implantable cardiac devices improve cardiac function in patients with heart disease thereby raising quality of life and reducing morality rates, implantable neurostimulators can provide pain reduction for chronic pain patients and reduce motor difficulties in patients with Parkinson's disease and other movement disorders. A variety of other medical devices are proposed and are in development to treat other disorders in a wide range of patients.

Neural activity can be influenced by electrical energy that is supplied from a stimulation system pulse generator or other waveform generator. Various patient perceptions and/or neural functions can be promoted, disrupted, or otherwise modified by applying an electrical pulses to target sites (the spinal cord, dorsal root ganglia, peripheral nerves, cortical locations, deep brain locations as examples). For example, spinal cord stimulation has been known to reduce pain levels for chronic pain patients for many years. Also, medical researchers and clinicians have attempted to treat various neurological conditions using electrical stimulation to control or affect brain functions. For example, Deep Brain Stimulation (DBS) may reduce some of the symptoms associated with Parkinson's Disease.

A stimulation system pulse generator may be provided in various configurations, such as an implanted pulse generator (IPG). A typical IPG configuration comprises a surgically implanted, internally-powered pulse generator and multi-electrode lead. The implanted pulse generator may commonly be encased in a hermetically sealed housing and surgically implanted in a subclavicular location. An electrode assembly may be implanted to deliver stimulation signals to a stimulation site. The electrode assembly is coupled to the pulse generator via biocompatibly sealed lead wires. A power source, such as a battery, is contained within the housing of the pulse generator.

SUMMARY

In some embodiments, a method of conducting operations with an implantable medical device (IMD) and an external controller device comprises performing authentication operations. In some embodiments, the method comprises: generating or storing an authentication data structure in the external controller device for over-the-air communication between the external device and the IMD, wherein the authentication data structure is generated by: (1) removing attribute fields from a first digital certificate and adding a public key of the external controller device to form an intermediate data structure; (2) creating a digital signature of the first intermediate data structure using a second digital certificate of an issuing certificate authority (CA); and (3) forming the authentication data structure by combining the intermediate data structure, the created digital signature, a public key of the issuing CA, and a digital signature of the public key of the issuing CA created using a third digital certificate of a root CA.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Neurostimulation systems are devices that generate electrical pulses and deliver the pulses to neural tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) which is often used to treat chronic pain such as Failed Back Surgery Syndrome (FBSS)

and Complex Regional Pain Syndrome (CRPS). Dorsal root ganglion (DRG) stimulation is another example of a neurostimulation therapy in which electrical stimulation is provided to the dorsal root ganglion structure that is just outside of the epidural space. DRG stimulation is generally used to treat chronic pain.

Neurostimulation systems generally include a pulse generator and one or more leads. A stimulation lead includes a lead body of insulative material that encloses wire conductors. The distal end of the stimulation lead includes multiple electrodes or contacts for application of electrical pulses to patient tissue. The electrodes or contacts are electrically coupled to the wire conductors of a respective stimulation lead. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Figure 1:
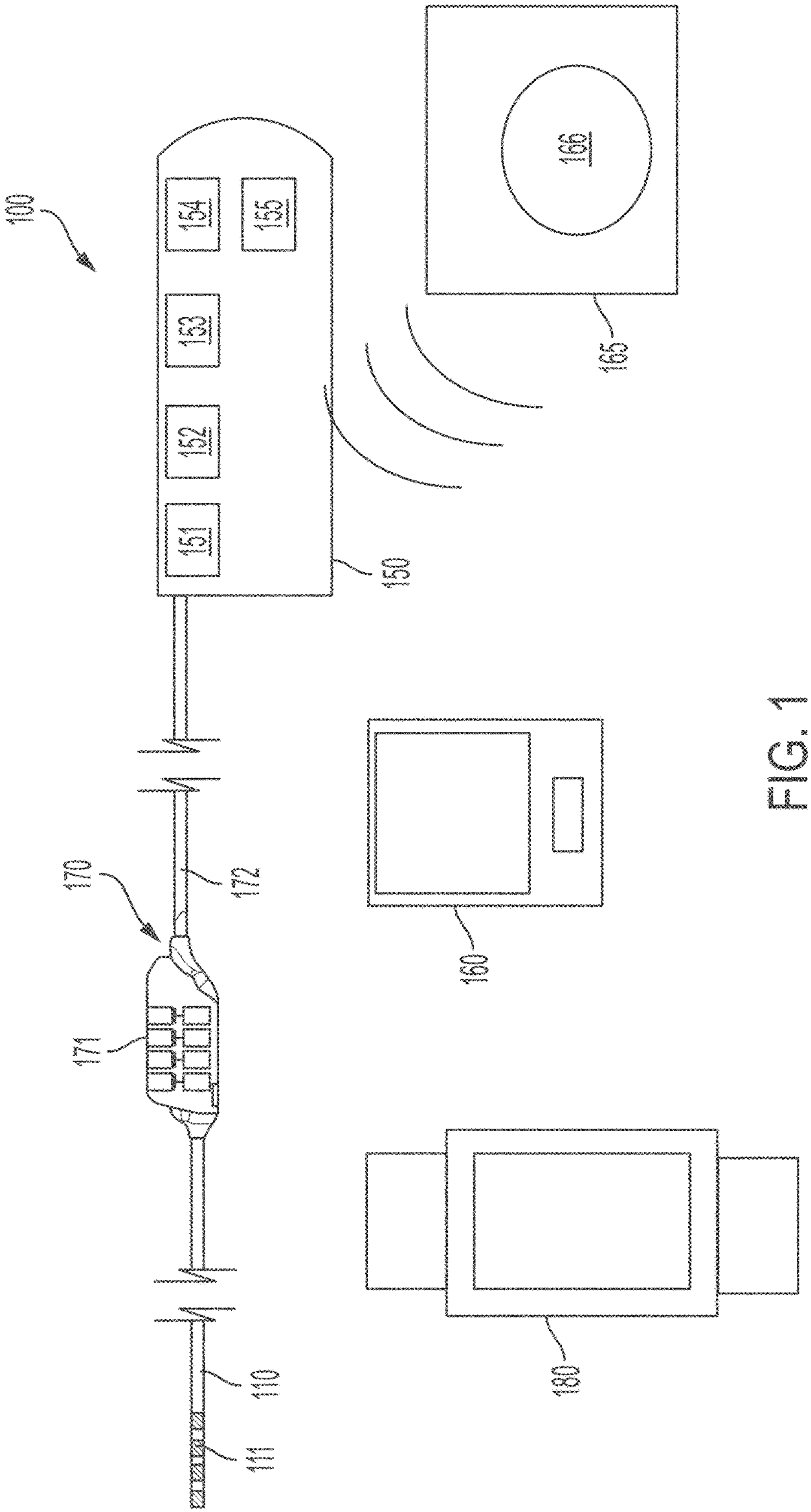
FIG. 1 depicts a neurostimulation system according to some embodiments.

Stimulation system 100 is shown in FIG. 1 according to some embodiments. Stimulation system 100 generates electrical pulses for application to tissue of a patient to treat one or more disorders of the patient. System 100 includes an implantable pulse generator (IPG) 150 that is adapted to generate electrical pulses for application to tissue of a patient. Examples of commercially available implantable pulse generators include the PROCLAIM XR™ and INFINITY™ implantable pulse generators (available from ABBOTT, PLANO TX). Commercially available IPGs may be adapted (using suitable software instructions, programmable parameters, logic circuits, other circuits, and/or the like) according to the disclosures in this application. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154 (e.g., BLUETOOTH communication circuitry), sensing circuitry 155, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, metal ribbons, traces, lines, or the like (not shown) from the internal circuitry of pulse generator 150 to output connectors (not shown) of pulse generator 150 which are typically contained in the "header" structure of pulse generator 150. Commercially available ring/spring electrical connectors are frequently employed for output connectors of pulse generators (e.g., "Bal-Seal" connectors). The terminals of one or more stimulation leads 110 are inserted within connector portion 171 for electrical connection with respective connectors or directly within the header structure of pulse generator 150. Thereby, the pulses originating from IPG 150 are conducted to electrodes 111 through wires contained within the lead body of lead 110. The electrical pulses are applied to tissue of a patient via electrodes 111.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

External controller device 160 is a device that permits the operations of IPG 150 to be controlled by a user after IPG 150 is implanted within a patient. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. The interface functionality of controller device 160 is implemented using suitable software code for interacting with the user and using the wireless communication capabilities to conduct communications with IPG 150. One or more user interface screens may be provided in software to allow the patient and/or the patient's clinician to control operations of IPG 150 using controller device 160. In some embodiments, commercially available devices such as APPLE IOS devices are adapted for use as controller device 160 by include one or more "apps" that communicate with IPG 150 using, for example, BLUETOOTH communication.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc.

Controller device 160 may permit programming of IPG 150 to provide a number of different stimulation patterns or therapies to the patient as appropriate for a given patient and/or disorder. Examples of different stimulation therapies include conventional tonic stimulation (continuous train of stimulation pulses at a fixed rate), BurstDR stimulation (burst of pulses repeated at a high rate interspersed with quiescent periods with or without duty cycling), "high frequency" stimulation (e.g., a continuous train of stimulation pulses at 10,000 Hz), noise stimulation (series of stimulation pulses with randomized pulse characteristics such as pulse amplitude to achieve a desired frequency domain profile). Any suitable stimulation pattern or combination thereof can be provided by IPG 150 according to some embodiments. Controller device 160 communicates the stimulation parameters and/or a series of pulse characteristics defining the pulse series to be applied to the patient to IPG 150 to generate the desired stimulation therapy.

Examples of suitable therapies include tonic stimulation (in which a fixed frequency pulse train) is generated, burst stimulation (in which bursts of multiple high frequency pulses) are generated which in turn are separated by quiescent periods, "high frequency" stimulation, multi-frequency stimulation, noise stimulation. Examples of suitable therapies include tonic stimulation (in which a fixed frequency pulse train) is generated, burst stimulation (in which bursts of multiple high frequency pulses) are generated which in turn are separated by quiescent periods, "high frequency" stimulation, multi-frequency stimulation, and noise stimulation. Descriptions of respective neurostimulation therapies are provided in the following publications: (1) Schu S., Slotty P. J., Bara G., von Knop M., Edgar D., Vesper J. A Prospective, Randomised, Double-blind, Placebo-controlled Study to Examine the Effectiveness of Burst Spinal Cord Stimulation Patterns for the Treatment of Failed Back Surgery Syndrome. Neuromodulation 2014; 17:443-450; (2) Al-Kaisy A1, Van Buyten J P, Smet I, Palmisani S, Pang D, Smith T. 2014. Sustained effectiveness of 10 KHz high-frequency spinal cord stimulation for patients with chronic, low back pain: 24-month results of a prospective multicenter study. Pain Med. 2014 March; 15 (3): 347-54; and (3) Sweet, Badjatiya, Tan D1, Miller. Paresthesia-Free High-Density Spinal Cord Stimulation for Postlaminectomy Syndrome in a Prescreened Population: A Prospective Case Series. Neuromodulation. 2016 April; 19 (3): 260-7. Noise stimulation is described in U.S. Pat. No. 8,682,441 B2. Burst stimulation is described in U.S. Pat. No. 8,224,453 and U.S. Published application No. 20060095088. A "coordinated reset" pulse pattern is applied to neuronal subpopulation/target sites to desynchronize neural activity in the subpopulations. Coordinated reset stimulation is described, for example, by Peter A. Tass et al in COORDINATED RESET HAS SUSTAINED AFTER EFFECTS IN PARKINSONIAN MONKEYS, Annals of Neurology, Volume 72, Issue 5, pages 816-820, November 2012, which is incorporated herein by reference. The electrical pulses in a coordinated reset pattern are generated in bursts of pulses with respective bursts being applied to tissue of the patient using different electrodes in a time-offset manner. The time-offset is selected such that the phase of the neural-subpopulations are reset in a substantially equidistant phase-offset manner. By resetting neuronal subpopulations in this manner, the population will transition to a desynchronized state by the interconnectivity between the neurons in the overall neuronal population. All of these references are incorporated herein by reference.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION" which is incorporated herein by reference.

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Examples of controller device 160 include patient controller (PC) devices and clinician programmer (PC) devices.

External charger device 165 may be provided to recharge battery 153 of IPG 150 according to some embodiments when IPG 150 includes a rechargeable battery. External charger device 165 comprises a power source and electrical circuitry (not shown) to drive current through coil 166. The patient places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. In operation during a charging session, external charger device 165 generates an AC-signal to drive current through coil 166 at a suitable frequency. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. IPG 150 may also communicate status messages to external charging device 165 during charging operations to control charging operations. For example, IPG 150 may communicate the coupling status, charging status, charge completion status, etc.

System 100 may include external wearable device 180 such as a smartwatch or health monitor device. Wearable device may be implemented using commercially available devices such as FITBIT VERSA SMARTWATCH™, SAMSUNG GALAXY SMARTWATCH™, and APPLE WATCH™ devices with one or more apps or appropriate software to interact with IPG 150 and/or controller device 160. In some embodiments, wearable device 180, controller device 160, and IPG 150 conduct communications using BLUETOOTH communications.

Wearable device 180 monitors activities of the patient and/or senses physiological signals. Wearable device 180 may track physical activity and/or patient movement through accelerometers. Wearable device 180 may monitory body temperature, heart rate, electrocardiogram activity, blood oxygen saturation, and/or the like. Wearable device 180 may monitor sleep quality or any other relevant health related activity.

Wearable device 180 may provide one or more user interface screens to permit the patient to control or otherwise interact with IPG 150. For example, the patient may increase or decrease stimulation amplitude, change stimulation programs, turn stimulation on or off, and/or the like using wearable device 180. Also, the patient may check the battery status of other implant status information using wearable device 180.

Wearable device 180 may include one or more interface screens to receive patient input. In some embodiments, wearable device 180 and/or controller device 160 are implemented (individually or in combination) to provide an electronic patient diary function. The patient diary function permits the patient to record on an ongoing basis the health status of the patient and the effectiveness of the therapy for the patient. In some embodiments as discussed herein, wearable device 180 and/or controller device 160 enable the user to indicate the current activity of the patient, the beginning of an activity, the completion of an activity, the ease or quality of patient's experience with a specific activity, the patient's experience of pain, the patient's experience of relief from pain by the stimulation, or any other relevant indication of patient health by the patient.

Figure 2:
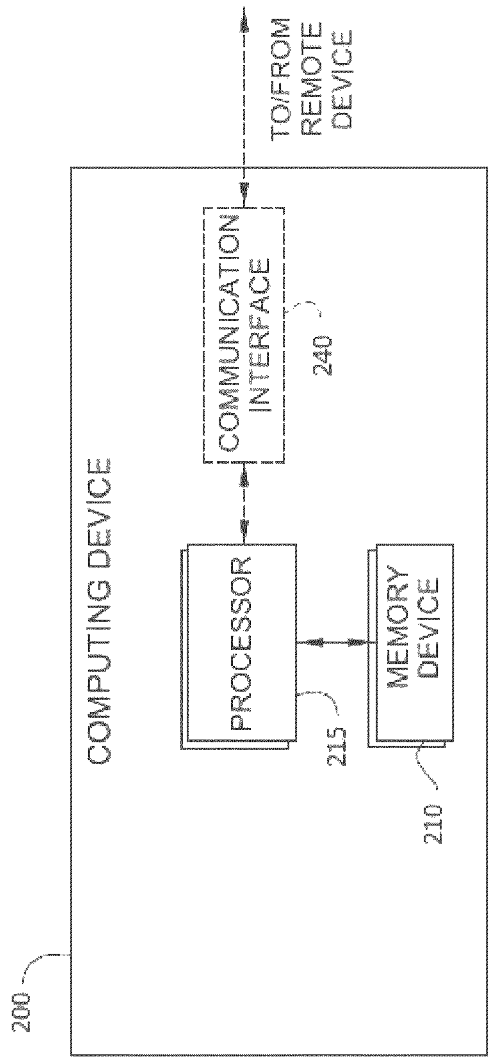
FIG. 2 depicts a computer system according to some embodiments.

FIG. 2 is a block diagram of one embodiment of a computing device 200 that may be used to according to some embodiments. Computing device 200 may be used to implement external controller device 160, wearable device 180, remote care management servers, or other computing system according to some embodiments.

Computing device 200 includes at least one memory device 210 and a processor 215 that is coupled to memory device 210 for executing instructions. In some embodiments, executable instructions are stored in memory device 210. In some embodiments, computing device 200 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 210 is one or more devices that enable information such as executable instructions and/or other data to be stored and retrieved. Memory device 210 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

Computing device 200, in the illustrated embodiment, includes a communication interface 240 coupled to processor 215. Communication interface 240 communicates with one or more remote devices, such as a clinician or patient programmer. To communicate with remote devices, communication interface 240 may include, for example, a wired network adapter, a wireless network adapter, a radio-frequency (RF) adapter, and/or a mobile telecommunications adapter.

Figure 3:
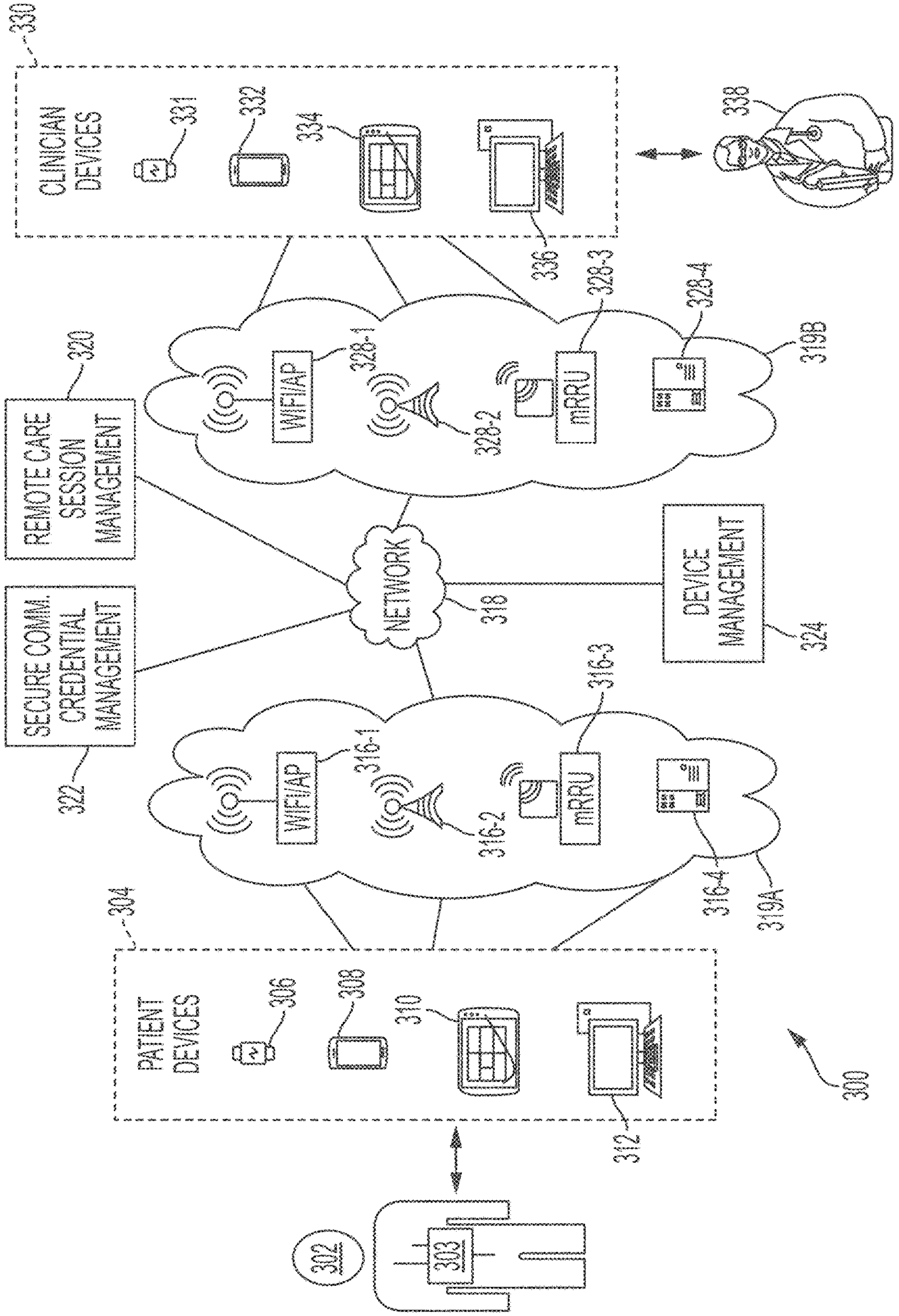
FIG. 3 depicts a system for monitoring and/or managing neurostimulation therapies for patients according to some embodiments.

FIG. 3 depicts a network environment 300 for remote management of patient care. One or more embodiments of a remote care therapy application or service may be implemented in network environment 300, as described herein. In general, "remote care therapy" may involve any care, biomedical monitoring, or therapy that may be provided by a clinician, a medical professional or a healthcare provider, and/or their respective authorized agents (including digital/virtual assistants), with respect to a patient over a communications network while the patient and the clinician/provider are not in close proximity to each other (e.g., not engaged in an in-person office visit or consultation). Accordingly, in some embodiments, a remote care therapy application may form a telemedicine or a telehealth application or service that not only allows healthcare professionals to use electronic communications to evaluate, diagnose and treat patients remotely, thereby facilitating efficiency as well as scalability, but also provides patients with relatively quick and convenient access to diversified medical expertise that may be geographically distributed over large areas or regions, via secure communications channels as described herein.

Network environment 300 may include any combination or sub-combination of a public packet-switched network infrastructure (e.g., the Internet or worldwide web, also sometimes referred to as the "cloud"), private packet-switched network infrastructures such as Intranets and enterprise networks, health service provider network infrastructures, and the like, any of which may span or involve a variety of access networks, backhaul and core networks in an end-to-end network architecture arrangement between one or more patients, e.g., patient(s) 302, and one or more authorized clinicians, healthcare professionals, or agents thereof, e.g., generally represented as caregiver(s) or clinician(s) 338.

Example patient(s) 302, each having a suitable implantable device 303, may be provided with a variety of corresponding external devices for controlling, programming, otherwise (re) configuring the functionality of respective implantable medical device(s) 303, as is known in the art. Such external devices associated with patient(s) 302 are referred to herein as patient devices 304 and may include a variety of user equipment (UE) devices, tethered or untethered, that may be configured to engage in remote care therapy sessions. By way of example, patient devices 304 may include smartphones, tablets or phablets, laptops/desktops, handheld/palmtop computers, wearable devices such as smart glasses and smart watches, personal digital assistant (PDA) devices, smart digital assistant devices, etc., any of which may operate in association with one or more virtual assistants, smart home/office appliances, smart TVs, virtual reality (VR), mixed reality (MR) or augmented reality (AR) devices, and the like, which are generally exemplified by wearable device(s) 306, smartphone(s) 308, tablet(s)/phablet(s) 310 and computer(s) 312. As such, patient devices 304 may include various types of communications circuitry or interfaces to effectuate wired or wireless communications, short-range and long-range frequency (RF) communications, magnetic field communications, Bluetooth communications, etc., using any combination of technologies, protocols, and the like, with external networked elements and/or respective implantable medical devices 303 corresponding to patient(s) 302.

With respect to networked communications, patient devices 304 may be configured, independently or in association with one or more digital/virtual assistants, smart home/premises appliances and/or home networks, to effectuate mobile communications using technologies such as Global System for Mobile Communications (GSM) radio access network (GRAN) technology, Enhanced Data Rates for Global System for Mobile Communications (GSM) Evolution (EDGE) network (GERAN) technology, 4G Long Term Evolution (LTE) technology, Fixed Wireless technology, 5th Generation Partnership Project (5GPP or 5G) technology, Integrated Digital Enhanced Network (IDEN) technology, WiMAX technology, various flavors of Code Division Multiple Access (CDMA) technology, heterogeneous access network technology, Universal Mobile Telecommunications System (UMTS) technology, Universal Terrestrial Radio Access Network (UTRAN) technology, All-IP Next Generation Network (NGN) technology, as well as technologies based on various flavors of IEEE 802.11 protocols (e.g., WiFi), and other access point (AP)-based technologies and microcell-based technologies such as femtocells, picocells, etc. Further, some embodiments of patient devices 104 may also include interface circuitry for effectuating network connectivity via satellite communications. Where tethered UE devices are provided as patient devices 304, networked communications may also involve broadband edge network infrastructures based on various flavors of Digital Subscriber Line (DSL) architectures and/or Data Over Cable Service Interface Specification (DOCSIS)-compliant Cable Modem Termination System (CMTS) network architectures (e.g., involving hybrid fiber-coaxial (HFC) physical connectivity). Accordingly, by way of illustration, an edge/access network portion 119A is exemplified with elements such as WiFi/AP node(s) 316-1, macro/microcell node(s) 116-2 and 116-3 (e.g., including micro remote radio units or RRUs, base stations, eNB nodes, etc.) and DSL/CMTS node(s) 316-4.

Similarly, clinicians 338 may be provided with a variety of external devices for controlling, programming, otherwise (re) configuring or providing therapy operations with respect to one or more patients 302 mediated via respective implantable medical device(s) 303, in a local therapy session and/or remote therapy session, depending on implementation and use case scenarios. External devices associated with clinicians 338, referred to herein as clinician devices 330, may include a variety of UE devices, tethered or untethered, similar to patient devices 304, which may be configured to engage in remote care therapy sessions as will be set forth in detail further below. Clinician devices 330 may therefore also include devices (which may operate in association with one or more virtual assistants, smart home/office appliances, VRAR virtual reality (VR) or augmented reality (AR) devices, and the like), generally exemplified by wearable device(s) 331, smartphone(s) 332, tablet(s)/phablet(s) 334 and computer(s) 336. Further, example clinician devices 330 may also include various types of network communications circuitry or interfaces similar to that of patient device 304, which may be configured to operate with a broad range of technologies as set forth above. Accordingly, an edge/access network portion 319B is exemplified as having elements such as WiFi/AP node(s) 328-1, macro/microcell node(s) 328-2 and 328-3 (e.g., including micro remote radio units or RRUs, base stations, eNB nodes, etc.) and DSL/CMTS node(s) 328-4. It should therefore be appreciated that edge/access network portions 319A, 319B may include all or any subset of wireless communication means, technologies and protocols for effectuating data communications with respect to an example embodiment of the systems and methods described herein.

In one arrangement, a plurality of network elements or nodes may be provided for facilitating a remote care therapy service involving one or more clinicians 338 and one or more patients 302, wherein such elements are hosted or otherwise operated by various stakeholders in a service deployment scenario depending on implementation (e.g., including one or more public clouds, private clouds, or any combination thereof). In one embodiment, a remote care session management node 320 is provided, and may be disposed as a cloud-based element coupled to network 318, that is operative in association with a secure communications credentials management node 322 and a device management node 324, to effectuate a trust-based communications overlay/tunneled infrastructure in network environment 300 whereby a clinician may advantageously engage in a remote care therapy session with a patient.

Additional details for remote programming and/or remote patient interaction are described in U.S Patent Application Pub. No. US20200398062A1, entitled "System, method and architecture for facilitating remote patient care," which is incorporated herein by reference.

In the embodiments described herein, implantable medical device 303 may be any suitable medical device. For example, implantable medical device may be a neurostimulation device that generates electrical pulses and delivers the pulses to nervous tissue of a patient to treat a variety of disorders. Other example implantable medical devices may include cardiac rhythm management devices (e.g., pacemakers, cardioverter defibrillator devices), cardiac monitoring devices, blood glucose monitoring devices, infusion/drug pumps, insulin pumps, and cochlear implants. Such devices may be adapted to employ the cybersecurity operations discussed herein to control privileged operations conducted with external devices. The privileged operations may include setting one or more operational parameters for operation of the IMD by the external device. The privileged operations may include modifying one or more therapy parameters for operation of the IMD that control a therapy provided by the IMD to the patient. The privileged operations may include communication of patient data (e.g., recorded physiological data of the patient) from the IMD to the external device.

Referring again to FIG. 1, IPG 150 and controller device 160 may communicate to control the patient's therapy and to conduct other operations. To protect the integrity of the patient's therapy and to protect data security, IPG 150 and controller device 160 may conduct respective security operations to ensure that only authorized applications on controller device 160 are able to communicate with and control operations of IPG 150.

In some embodiments, there may be processing and/or communication limitations for IPG 150 and/or controller 160. Some embodiments compress the PKI implementation for authentication for implantable device communication and control and minimize data sent over the air. In some embodiments, IPG 150 and/or controller 160 employ PKI-based methods that are more flexible for transport types that may have limited data rates and cannot support the size of standard X.509 certificates in a more optimally efficient manner. These methods are transport-agnostic and can be used over low-rate wireless (such BLE that has lower power and transmit characteristics, or inductive wireless communication) or low-rate wired communication paths. By employing such authentication methods, some embodiments improve cybersecurity of implantable medical device systems for a wider range of an implant devices.

In an implanted medical device context, not all attributes of an X.509 certificate are relevant for decision-making or authentication with an implantable medical device. The key components for validating a chain of trust back to shared root are based in the public key of the root and the data signed by the root's corresponding private key. This makes much of the standard X.509 certificate design superfluous in medical device context.

In some embodiments, a method for medical device cybersecurity extracts and signs only the relevant data from the standard X.509 certificates, thus minimizing the total data involved in each transaction and by extension minimizing the amount of data sent over the air between a medical device and external entity such as a programmer. This reduces the amount of time needed to exert control over the device (which could be critical in life-sustaining devices) and also reduces the power burden of the implanted medical device for secure communications (extending the life of the device in comparison to a standard PKI-based approach).

Figure 4:
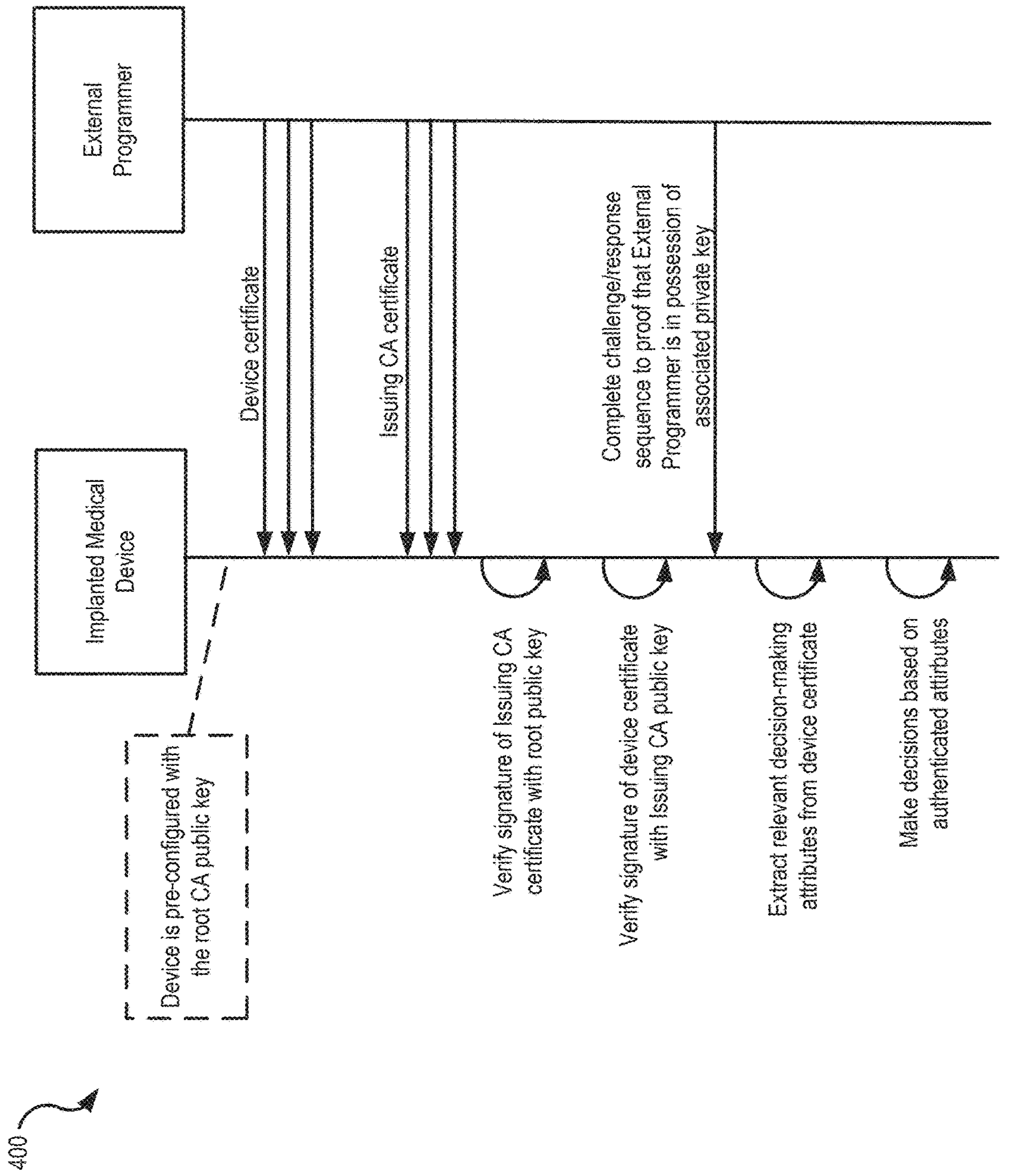
FIG. 4 depicts authentication operations using PKI digital certificates.

Referring now to FIG. 4, in a different (but not prior art) PKI based approach for implanted medical devices, a full chain of X.509 certificates are used to provide machine-to-machine authentication as shown in authentication operations 400. The medical device is pre-configured with the public key of a root certificate authority (CA); any external entity attempting to authenticate to the medical device must present a certificate that is signed in a chain that is verifiable back to that root CA.

This generally involves at least one intermediary Issuing Certificate Authority—the external entity presents its certificate, which is signed by the Issuing CA—the external entity then also presents the Issuing CA's certificate, which is itself signed by the root CA. In this way, the medical device can verify each X.509 certificate in the chain back to the root of trust.

The challenge of using this approach over a low-rate communication path is that X.509 formatted certificates are designed for TCP/IP networks and as such assume no tangible constraints on data rates. As a result, they can be too large to effectively transfer over a rate-limited communication transport (e.g., 2 KB or larger). The programmer or other external device must send both full certificates over the air; the implanted medical device then verifies that the Issuing CA's certificate is signed by the Root CA, and that the Device certificate is signed by the Issuing CA. It also verifies that the programmer or other external device is in possession of the private key corresponding to its public key.

Once this sequence is complete, the implantable medical device can extract the relevant attributes from the programmer's authenticated certificate and then can make decisions based on those attributes.

Figure 5:
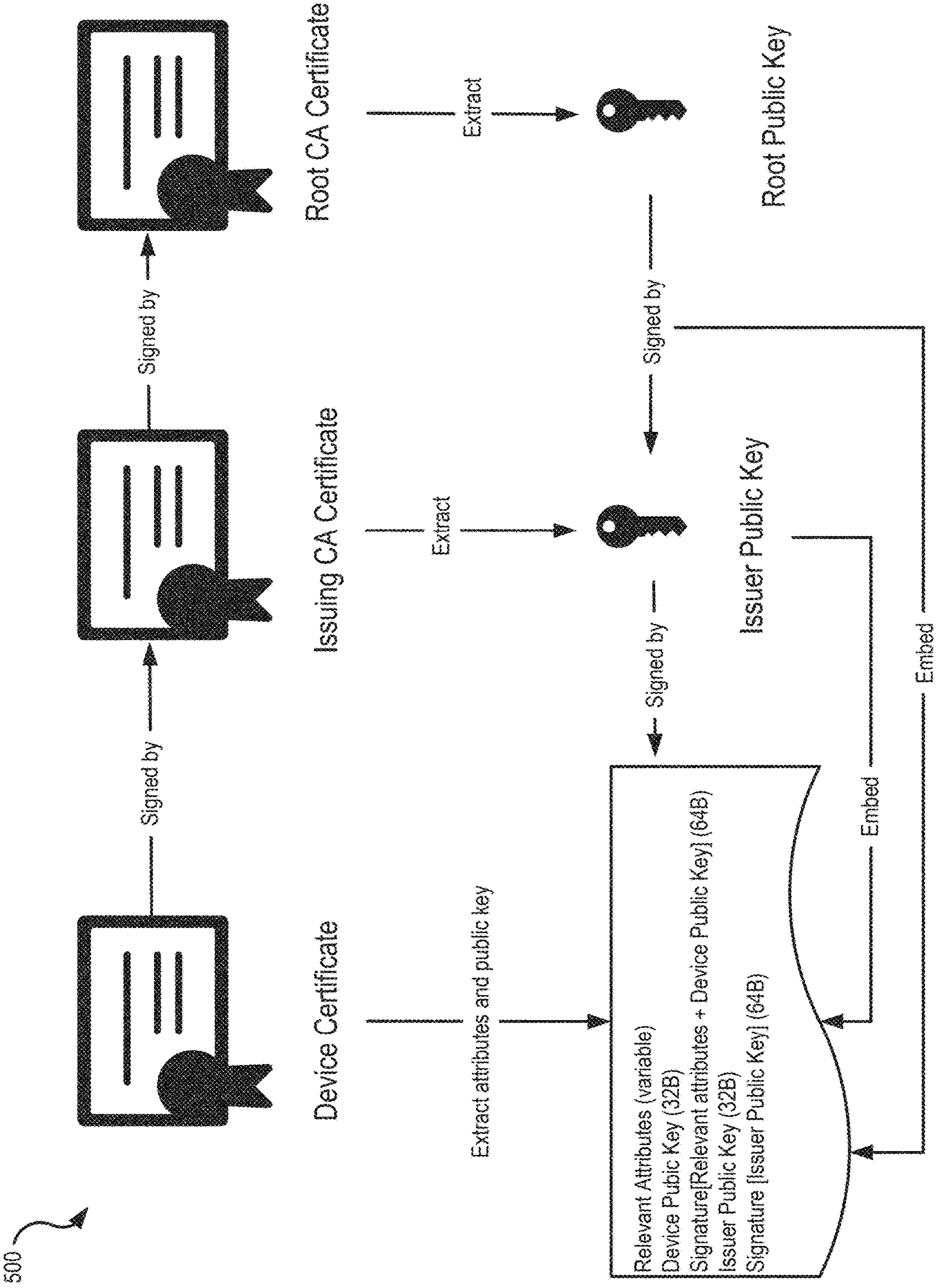
FIGS. 5 and 6 depict security data structures and authentication operations for an implantable medical device and an external device according to some embodiments.

Referring now to FIG. 5, to still use a chain of trust, but to minimize the data that must be transferred over the low-rate communication path, there is an alternate approach that modifies the authentication operations 400 (previously shown in FIG. 4). In some embodiments, the focus is on the public keys and relevant decision-making attributes of the X.509 of the external entity attempting to authenticate to the medical device. In any given permutation of such a medical device, not all attributes of the external entity's X.509 certificate or of the issuing CA's X.509 certificate are relevant for decision-making—the medical device's design may specify only a subset of attributes that are needed, and the other attributes may be defined as extraneous. Data structures 500 as shown in FIG. 5 may be defined to manage the data transferred for authentication operations according to some embodiments.

Figure 6:
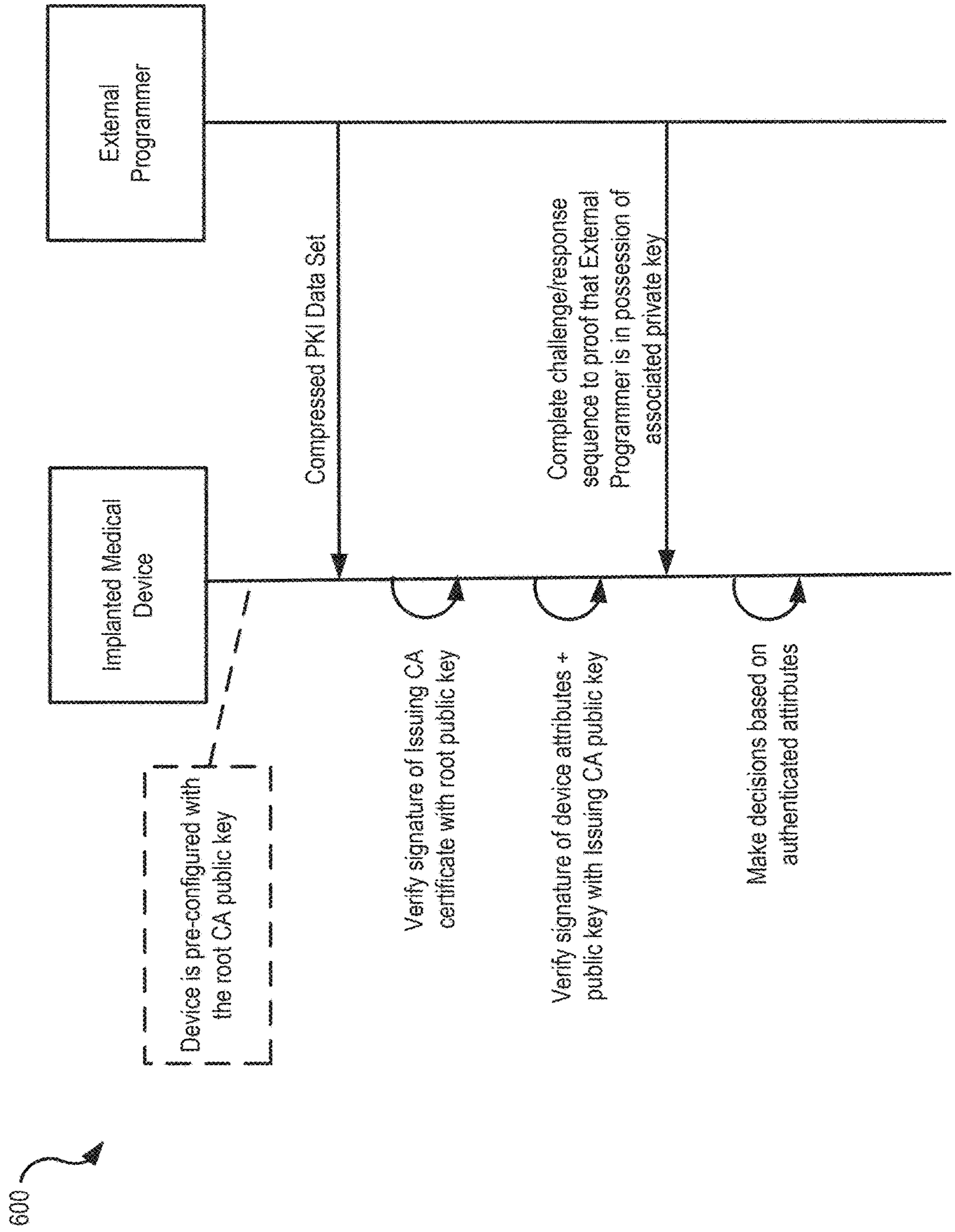

In some embodiments, one or more of the following changes are introduced for data structures 500 when creating/provisioning certificates on the external device: (1) the relevant attributes are defined and extracted from the X.509 certificate into a new data structure (which may be of any format such as raw binary to minimize overhead in the data structure) along with the device's public key; (2) those relevant attributes and device public key are signed by the Issuing CA, this signature data is also included the new data structure; (3) the Issuing CA's public key is signed by the Root CA; and (4) both the Issuing CA's public key, and the signature of that public key by the Root CA are included in the new data structure In some embodiments, when authenticating to the medical device, rather than sending a full certificate chain, the external entity sends only this data structure containing the relevant data to the medical device. Referring now to authentication operations 600 in FIG. 6, rather than performing verification of an X.509 certificate chain, the implantable medical device may verify one or more of the following: (1) the public key of the Issuing CA is signed by the public key of the root CA; (2) the device's public key and attributes are signed by the public key of the Issuing CA; (3) the device is in possession of the private key corresponding to its public key; and (4) once this sequence is complete, the implantable medical device can consider the attributes to be authenticated and can make decisions based on those attributes.

Verification of possession of the private key may occur using known or new operations. For example, the IMD may encrypt a secret value (e.g., a random number) using the public key and the external device decrypts it using the private key. The IMD may, then in turn, encrypt the random number of with the public key of the IMD and return that value to the IMD. The IMD verifies the possession of the private key by the external device by decrypting this value with the private key of the IMD. Other challenge/response exchanges are known and may be used for this purpose.

In some embodiments, the medical device minimizes the data sent over the air by deviating from the standard X.509 format, but still verifies the authentication data back to the root of trust.

In some embodiments, in one example implementation in which both the external entity's X.509 certificate and the Issuing CA's certificate are 2 KB for a combined total of 4 KB of data from the external entity to the medical device, this method could result in the amount of data being sent over the air being reduced to 192 B plus the length of the defined relevant attributes: (1) relevant decision-making attributes: variable; (2) device public key: 32 B; (3) signature of device public key and relevant attributes by Issuing CA: 64 B; (4) issuing CA public key: 32 B; (5) signature of Issuing CA public key by Root CA: 64 B.

In some embodiments, with an example of 512 B of relevant attributes, the total amount of authentication data sent to the medical device could be as little as 704 B instead of 4 KB (a reduction of 85% compared to a non-compressed PKI approach) while still maintaining the chain of trust to a shared root. This reduction in over-the-air data reduces the amount of time needed to connect the device and subsequently exert control over it (which could be critical in life-sustaining devices). It also reduces the power burden of the implanted medical device for secure communications (thus extending the life of the device battery in comparison to a standard PKI-based approach).

IPG 150, external controller device 160, and/or wearable device 180 may be adapted to perform the operations discussed herein. For example, suitable firmware/software code may be stored in the respective device to define the operations discussed herein to perform security/authentication operations before permitting or allowing privileged medical device operations.

Figure 7:
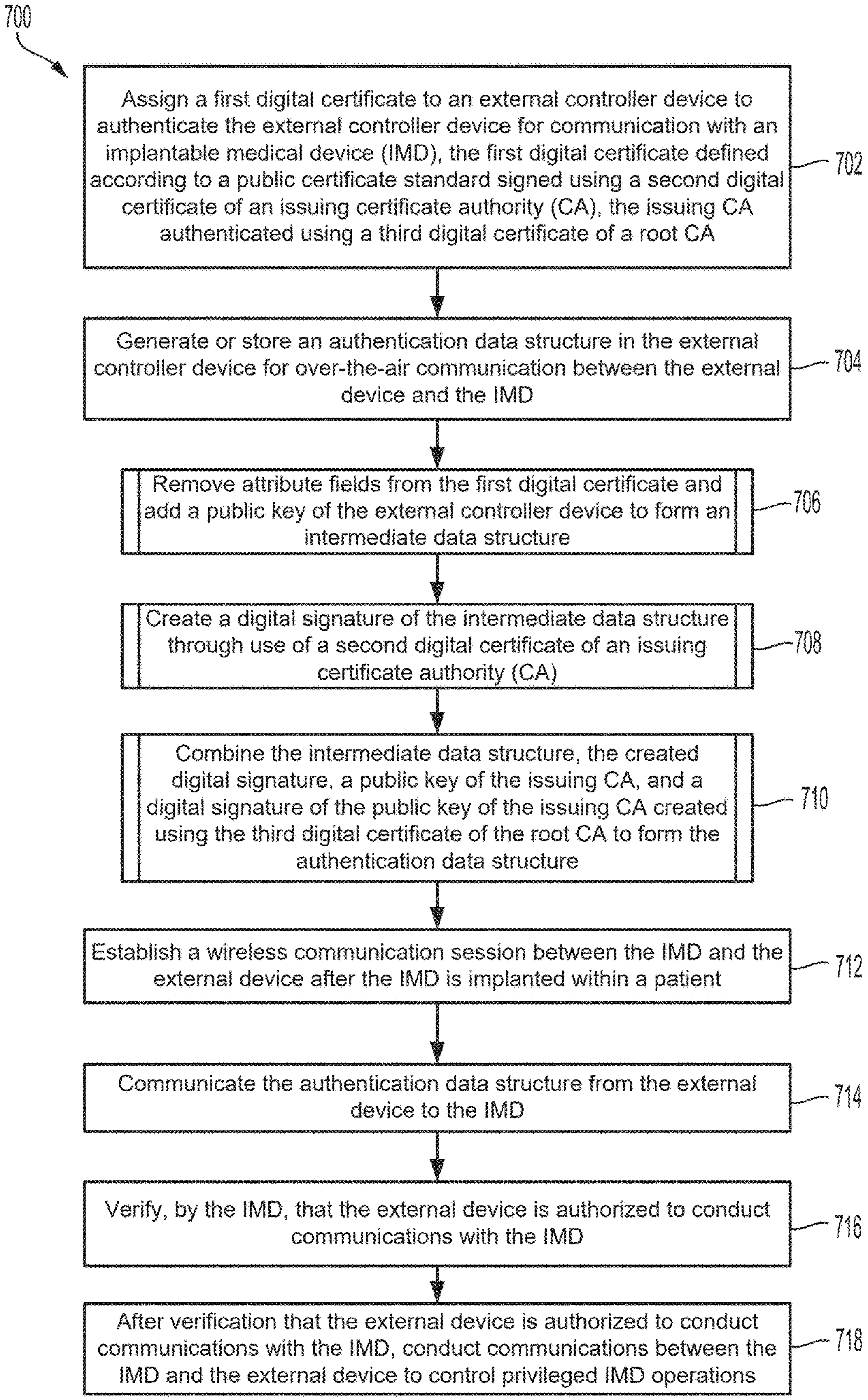
FIG. 7 is a flow chart of an example method for conducting operations with an implantable medical device (IMD) and an external controller device according to some embodiments.

Referring to FIG. 7, a flow chart of an example method 700 for conducting operations with an implantable medical device (IMD) and an external controller device according to some embodiments is depicted. At block 702, a first digital certificate may be assigned to an external controller device to authenticate the external controller device for communication with an IMD. The first digital certificate may be defined according to a public certificate standard signed using a second digital certificate of an issuing certificate authority (CA). The issuing CA may be authenticated using a third digital certificate of a root CA.

At block 704, an authentication data structure may be generated or stored in the external controller device for over-the-air communication between the external device and the IMD. The authentication data structure may be generated in accordance with blocks 706-710. For example, at block 706, attribute fields may be removed from the first digital certificate and a public key of the external controller device may be added to form an intermediate data structure. At block 708, a digital signature of the intermediate data structure may be created through use of a second digital certificate of an issuing certificate authority (CA). At block 710, the intermediate data structure, the created digital signature, a public key of the issuing CA, and a digital signature of the public key of the issuing CA created using the third digital certificate of the root CA may be combined to form the authentication data structure.

At block 712, a wireless communication session may be established between the IMD and the external device after the IMD is implanted in the patient. At block 714, the authentication data structure (e.g., formed via blocks 706-710) may be communicated from the external device to the IMD. At block 716, the IMD may verify that the external device is authorized to conduction communications with the IMD. At block 718, after verification that the external device is authorized to conduct communications with the IMD, communications may be conducted between the IMD and the external device to control privileged IMD operations.

Although the aspects of the present disclosure and their advantages have been described in detail, it should be understood that various changes, substitutions and alterations can be made herein without departing from the spirit of the disclosure as defined by the appended claims. Moreover, the scope of the present application is not intended to be limited to the particular implementations of the process, machine, manufacture, composition of matter, means, methods and processes described in the specification. As one of ordinary skill in the art will readily appreciate from the present disclosure, processes, machines, manufacture, compositions of matter, means, methods, or operations, presently existing or later to be developed that perform substantially the same function or achieve substantially the same result as the corresponding aspects described herein may be utilized according to the present disclosure. Accordingly, the appended claims are intended to include within their scope such processes, machines, manufacture, compositions of matter, means, methods, or operations.

The invention claimed is:

1. A method of conducting operations with an implantable medical device (IMD) and an external controller device, the method comprising:

generating or storing an authentication data structure in the external controller device, the authentication data structure is generated by:

removing one or more attribute fields from a first digital certificate assigned to the external controller device and adding a public key of the external controller device to form an intermediate data structure;

creating a digital signature of the intermediate data structure by using a second digital certificate, resulting in a created digital signature; and forming the authentication data structure by combining the intermediate data structure, the created digital signature, a public key of an issuing certificate authority (CA), and a digital signature of the public key; and using the authentication data structure to conduct communications between the IMD and the external controller device.

2. The method of claim 1, wherein the using of the authentication data structure to conduct communications between the IMD and the external controller device includes controlling, with the external controller device, privileged IMD operations.

3. The method of claim 1, wherein the communications between the IMD and the external controller device include over-the-air communications.

4. The method of claim 1, wherein the first digital certificate is defined according to a public certificate standard and is signed using the second digital certificate of the issuing CA.

5. The method of claim 1, wherein the issuing CA is authenticated using a third digital certificate of a root CA.

6. The method of claim 1, wherein the created digital signature of the intermediate data structure is created using the second digital certificate of the issuing CA.

7. The method of claim 1, further comprising establishing a wireless communication session between the IMD and the external controller device after the IMD is implanted within a patient.

8. The method of claim 1, further comprising communicating the authentication data structure from the external controller device to the IMD.

9. The method of claim 1, wherein the conducting of communications between the IMD and the external controller device is responsive to verifying, at the IMD, that the external controller device is authorized to conduct the communications with the IMD.

10. A method of conducting operations with an implantable medical device (IMD) and an external controller device, the method comprising:

receiving an authentication data structure at the IMD, the authentication data structure is generated by:

removing one or more attribute fields from a first digital certificate assigned to the external controller device and adding a public key of the external controller device to form an intermediate data structure;

creating a digital signature of the intermediate data structure by using a second digital certificate, resulting in a created digital signature; and forming the authentication data structure by combining the intermediate data structure, the created digital signature, a public key of an issuing certificate authority (CA), and a digital signature of the public key; and initiating communications between the IMD and the external controller device in response to the receiving of the authentication data structure at the IMD.

11. The method of claim 10, wherein the authentication data structure is received at the IMD from the external controller device.

12. The method of claim 10, further comprising controlling, with the communications between the IMD and the external controller device, privileged IMD operations.

13. The method of claim 12, wherein the controlling of the privileged IMD operations includes setting one or more operational parameters of the IMD.

14. The method of claim 13, wherein the controlling of the privileged IMD operations includes modifying one or more therapy parameters for operation of the IMD that control a therapy provided by the IMD to a patient.

15. The method of claim 14, wherein the therapy parameters include one or more stimulation parameters for a neurostimulation therapy including at least one of: spinal cord stimulation, dorsal root ganglion stimulation, peripheral nerve stimulation, cortical stimulation, or deep brain stimulation.

16. The method of claim 12, wherein the privileged IMD operations include receiving patient data from the IMD by the external controller device.

17. The method of claim 11, further comprising verifying, by the IMD, that the external controller device is authorized to conduct communications with the IMD, the verifying is performed without sending a full certificate chain to the IMD.

18. The method of claim 10, further comprising analyzing, by the IMD, permissions contained in the authentication data structure to identify privileged IMD operations permitted by the external controller device.

19. A method of conducting operations with an implantable medical device (IMD) and an external controller device, the method comprising:

receiving an authentication data structure at the IMD, the authentication data structure is generated by:

removing one or more attribute fields from a first digital certificate assigned to the external controller device and adding a public key of the external controller device to form an intermediate data structure;

creating a digital signature of the intermediate data structure by using a second digital certificate, resulting in a created digital signature; and forming the authentication data structure by combining the intermediate data structure, the created digital signature, a public key of an issuing certificate authority (CA), and a digital signature of the public key; and conducting communications between the IMD and the external controller device, in response to the receiving of the authentication data structure at the IMD, the communications setting one or more therapy stimulation parameters of the IMD.

20. The method of claim 19, wherein the one or more therapy stimulation parameters include at least one of:

a pulse amplitude;

a pulse width;

a pulse frequency;

an inter-pulse period; or a pulse repetition parameter.

* * * * *